(12) United States Patent
Yokoi

(10) Patent No.: US 7,338,809 B2
(45) Date of Patent: Mar. 4, 2008

(54) METHOD FOR ASSAYING WHOLE BLOOD

(75) Inventor: Hiroyuki Yokoi, Tokyo (JP)

(73) Assignee: Mitsubishi Kagaku Iatron, Inc., Tokyo (JP)

( * ) Notice: Subject to any disclaimer, the term of this patent is extended or adjusted under 35 U.S.C. 154(b) by 513 days.

(21) Appl. No.: 10/657,118

(22) Filed: Sep. 9, 2003

(65) Prior Publication Data

US 2004/0048397 A1    Mar. 11, 2004

Related U.S. Application Data

(63) Continuation of application No. PCT/JP02/02139, filed on Mar. 7, 2002.

(30) Foreign Application Priority Data

Mar. 9, 2001    (JP) .............................. 2001-067360

(51) Int. Cl.
*G01N 1/00*    (2006.01)

(52) U.S. Cl. ...................... 436/176; 435/7.1; 435/7.25; 435/7.92; 435/7.94; 436/517; 436/518; 436/522; 436/524; 436/528; 436/538; 436/10; 436/17; 436/18; 436/166; 422/61

(58) Field of Classification Search .................... 435/2, 435/7.1, 7.24, 7.25, 7.92, 7.94, 173.9, 297.2, 435/339; 436/517, 518, 524, 526, 528, 538, 436/10, 17, 18, 172, 808, 522, 166, 176; 422/61

See application file for complete search history.

(56) References Cited

U.S. PATENT DOCUMENTS

| 4,313,927 | A | * | 2/1982 | Fridlender ...................... 435/5 |
| 5,284,771 | A | | 2/1994 | Fan et al. |
| 5,633,167 | A | | 5/1997 | Fan et al. |
| 6,030,845 | A | | 2/2000 | Yamao et al. |
| 6,103,537 | A | * | 8/2000 | Ullman et al. ............... 436/526 |
| 6,143,510 | A | * | 11/2000 | Hoshino et al. ............ 435/7.94 |
| 6,194,219 | B1 | * | 2/2001 | Sakamoto et al. .......... 436/166 |
| 6,280,618 | B2 | * | 8/2001 | Watkins et al. .............. 210/222 |

FOREIGN PATENT DOCUMENTS

| EP | 0 545 313 | 6/1993 |
| EP | 0 722 087 | 7/1996 |
| EP | 0 822 412 | 2/1998 |
| JP | 6-167495 | 6/1994 |
| JP | 6-265554 | 9/1994 |
| JP | 09-072902 | 3/1997 |
| JP | 9-274041 | 10/1997 |
| JP | 09-274041 | 10/1997 |
| JP | 10-48214 | 2/1998 |
| JP | 2711786 | 2/1998 |
| JP | 2000-065830 | 3/2000 |
| JP | 2000-65830 | 3/2000 |
| JP | 2000-508075 | 6/2000 |
| WO | WO 96/04558 | 2/1996 |
| WO | WO 98/30908 | 7/1998 |

OTHER PUBLICATIONS

M. J. Benecky, et al., Clinical Chemistry, vol. 43, No. 9, pp. 1764-1770, "Detection of Hepatitis B Surface Antigen in Whole Blood by Coupled Particle Light Scattering (Copalis)", 1997.

Takuya Hasegawa et al, "Evaluation of an ODS Column Modified with Zwitterionic/Nonionic Mixed Surfactants and Its Application to Direct Injection Determination of Inorganic Anions", *Analytical Sciences*, Aug. 2005, vol. 21, pp. 913-916.

Leonard M. Hjelmeland, "A nondenaturing zwitterionic detergent for membrane biochemistry: Design and synthesis", *Proc. Natl. Acad. Sci. USA*, Nov. 1980, vol. 77, No. 11, pp. 6368-6370.

Gopi N. Devaraj et al, "Release Studies on Niosomes Containing Fatty Alcohols as Bilayer Stabilizers Instead of Cholesterol", *Journal of Colloid and Interface Science*, 2002, vol. 251, pp. 360-365.

\* cited by examiner

*Primary Examiner*—Gailene Rio Gabel
(74) *Attorney, Agent, or Firm*—Oblon, Spivak, McClelland, Maier & Neustadt, P.C.

(57) ABSTRACT

In a method for measuring an analyte, which comprises a reaction step of forming a reaction system including a sample containing whole blood, a first substance carried by a solid carrier and specifically binding to an analyte contained in the sample and a second substance specifically binding to the analyte and allowing the analyte to react with the first and second substances and a measurement step of measuring the formed reaction product, (1) the reaction step is performed in a state that blood cells are not disrupted, and (2) at least the reaction step is performed in the presence of a sufficient amount of a detergent that does not cause hemolysis, does not inhibit reactions of the analyte with the first and second substances specifically binding to the analyte and can prevent influence on the reaction system of a component existing in the reaction system.

7 Claims, No Drawings

METHOD FOR ASSAYING WHOLE BLOOD

CROSS REFERENCES TO RELATED APPLICATIONS

This application is a continuation of International Patent Application No. PCT/JP02/02139, filed on Mar. 7, 2002, and claims priority to Japanese Patent Application No. 2001-67360, filed on Mar. 9, 2001.

TECHNICAL FIELD

The present invention relates to a method for analyzing a particular component contained in whole blood in which whole blood is used as a sample.

BACKGROUND ART

Measurement of components in blood, for example, antigens, antibodies, proteins, endocrine substances and so froth is clinically very important. In general, plasma or serum is used as a blood sample in many cases, and in such cases, whole blood is usually separated into serum or plasma as quickly as possible in order to avoid hemolysis. This is because, for example, in the field of immunological tests, if hemocytic components are present or hemolysis is caused in a sample, there may be caused disturbing phenomena such as influence of hemolysis on optical systems, inhibition of immunological reaction by internal components of blood cells and aggregation or adhesion of cytoplasmic membrane components of blood cells on an solid carrier used as a solid phase. Therefore, in ordinary clinical tests, it has been a common practice that extracted whole blood is first centrifuged to remove blood cells, and the obtained plasma or serum is used as a sample for measurement.

However, in order to remove blood cells, dedicated instruments such as centrifugal machine are required, and the operation is laborious. Therefore, it is desirable to use whole blood as it is as a measurement sample for physician in practice who do not have such installations and urgent tests with scarce temporal margin.

To satisfy the above requirements, there have been already proposed various methods of assaying whole blood itself without separating serum or plasma. As for immunoassay, a method utilizing latex coagulation as a homogeneous assay (method not requiring B/F separation) has been reported as a measurement method in which hemolysis of blood cells is intentionally and forcibly caused (Japanese Patent Laid-open Publication (Kokai) No. 10-48214). Secondly, as assay methods without causing hemolysis of blood cells, a homogeneous assay method using latex scattered light (clinical Chemistry, Vol. 43, 1764-1770 (1997)), a heterogeneous assay method (method requiring B/F separation) using a plastic cuvette as a solid phase (Japanese Patent Laid-open Publication No. 6-265554) and a method using polystyrene beads or magnetic particles as a solid phase (International Patent Unexamined Publication in Japanese (Kohyo) No. 2000-508075, WO96/04558) have been reported.

However, it cannot be said that convenient and highly sensitive assay methods using whole blood as a sample have already been established even by using these methods. First, even though some immunoassays using a homogeneous assay have been reported as convenient methods, an analyte is often a substance contained in blood in a trace amount in clinical tests and so forth, and therefore it is generally more strongly required to assay whole blood by using a heterogeneous assay that theoretically enables a highly sensitive assay. Secondly, with the background that solid carriers such as magnetic particles are widely used in a heterogeneous assay as a solid phase because of simplicity of B/F separation, micro particles such as magnetic particles are likely to be influenced by, in particular, blood cells, although solid carriers having a such size that the solid carriers should not aggregate causes no problem as in the cases of beads having a diameter of millimeter order and plastic plates. For example, when hemolysis occurs, inhibitory substances such as hemoglobin and cell nucleus-derived substances flowing out of the inside of blood cells into a reaction system may cause non-specific aggregation of solid carriers or reduce immune reaction, thereby seriously affecting the assay. Further, even when fresh unhemolyzed whole blood is used as a sample, if blood cells exist, solid carriers becomes likely to easily adhere on an inner wall of reaction vessel or a pipette tip due to blood cell membrane surface substances or the like, and thus harms such as inaccurate assay may be caused.

Moreover, instruments and cartridges for automatic assay are often used so as to quickly and conveniently conduct such assays of whole blood as described above. However, similar problems also occur in each step of such automatic assays. That is, since blood cell components in whole blood and solid carriers used for the assays are precipitated with time, it is essential to include a step of sufficiently stirring a sample containing whole blood prior to the assays so as to maintain blood cell components uniform or sufficiently stirring the sample, solid carrier, reagents etc. in a reaction step or assay step. In such a stirring step, a strong force is imposed on blood cells, and blood cells are disrupted, resulting in extremely easy hemolysis. Further, since suction and discharge of sample are performed in each step for successively transferring the sample to target reaction vessels following the steps, a strong force is imposed on blood cells and thus hemolysis easily occurs. In addition, non-specific adhesion and aggregation also easily occurs. Therefore, assay errors may be often caused.

In recent years, such instruments and cartridges for automatic assays as described above are also widely used in the field of point of care testing (POCT), which draws attentions as emergency test or test readily conducted by physicians and nurses. Accordingly, development of an assay method that can provide correct assay results even by an assay using such equipments and whole blood as it is has been required.

DISCLOSURE OF THE INVENTION

An object of the present invention is to provide means for quickly and conveniently assaying an analyte in whole blood with high sensitivity by using the whole blood as it is as a sample.

The inventors of the present invention conducted various studies in order to achieve the aforementioned object. As a result, they found that, in a method for measuring an analyte contained in a sample containing whole blood, if a reaction was proceeded in the presence of a detergent and in a state that blood cells are not disrupted, the measurement could be conducted in a short period of time with high sensitivity without performing serum/plasma separation by centrifugation or the like.

Thus, the present invention provides a method for measuring an analyte, which comprises a reaction step of forming a reaction system including a sample containing whole blood, a first substance carried by a solid carrier and specifically binding to an analyte contained in the sample and a second substance specifically binding to the analyte and allowing the analyte to react with the first and second substances and an assay step of assaying a formed reaction product, wherein (1) the reaction step is performed in a state that blood cells are not disrupted, and (2) at least the reaction step is performed in the presence of a sufficient amount of detergent that does not cause hemolysis, does not inhibit reactions of the analyte with the first and second substances specifically binding to the analyte and can prevent influence on the reaction system of a component existing in the reaction system.

Further, another embodiment of the present invention is a method for measuring an analyte in whole blood, which comprises:
(1) a dilution step of diluting whole blood by mixing the whole blood with a whole blood treatment solution;
(2) a first reaction step of adding a first substance carried by a solid carrier and specifically binding to the analyte to the diluted whole blood and allowing them to react to form a first reaction product in a reaction system;
(3) a first separation step of separating the first reaction product formed in the first reaction step from the reaction system;
(4) a second reaction step of adding a second substance specifically binding to the analyte to the separated first reaction product and allowing them to react to form a second reaction product in a reaction system;
(5) a second separation step of separating the second reaction product formed in the second reaction step from the reaction system; and
(6) a measurement step of measuring the separated second reaction product, wherein
the whole blood treatment solution contains a sufficient amount of detergent that does not cause hemolysis, does not inhibit reactions of the analyte with the first and second substances, and can prevent influence on the reaction system of a component existing in the reaction system in each step when the solution is mixed with the whole blood.

Further, from another aspect of the present invention, there is provided a reagent kit used in the measurement method of the present invention. An embodiment of the reagent kit is a reagent kit for measuring an analyte in whole blood, which comprises a first substance carried by a solid carrier and specifically binding to the analyte, a second substance specifically binding to the analyte and a detergent which does not cause hemolysis when it is mixed with whole blood and does not inhibit reactions of the analyte with the first substance and the second substance.

Hereafter, the present invention will be explained in detail.

The measurement method of the present invention is a method for measuring an analyte in a sample containing whole blood.

The term "sample containing whole blood" means whole blood collected from a patient as it is, whole blood mixed with a certain treatment solution (henceforth also referred to as "whole blood treatment solution") or the like. The term "whole blood" means whole blood collected from a patient on the assumption that it contains an analyte or may contain the analyte, and fresh blood is used preferably within 3 days after collection, more preferably within 24 hours after collection, further preferably immediately after collection or within 12 hours after collection. Blood can be collected by a known method using a blood collection tube or the like treated with an anticoagulant such as EDTA or heparin. Blood is preferably stored by cold storage, more preferably at 4 to 0° C.

The analyte is not particularly limited so long as it is contained in whole blood and is a substance for which a substance specifically binding to it to form a reaction product exists. Examples of a combination of the analyte and the substance specifically binding to it include antigen and antibody, antibody and antigen, protein and ligand, sugar chain and lectin and so forth. Particularly preferred are antigen and antibody or antibody and antigen. Thus, in the present invention, the term "specifically binding to" means forming a reaction product through a biochemically specific bond. Specific examples of the analyte include hepatitis B virus surface antigen (HBsAg), hepatitis C virus (HCV) antibody and antigen, human immunodeficiency virus (HIV) antibody, human T cell leukemia virus-1 (HTLV-1) antibody, Treponema pallidum (TP) antibody and so forth. Further, various cardiac muscle markers (creatine kinase (CKMB), myoglobin, troponin), various hormones, serum proteins and so forth can also be mentioned.

Further, the measurement method of the present invention is a heterogeneous assay using a first substance carried by a solid carrier and specifically binding to an analyte and a second substance specifically binding to the analyte. Such a method may be any method so long as it comprises a reaction step of allowing the aforementioned analyte in a sample containing whole blood to react with the first and second substances and a measurement step of measuring the formed reaction product.

Specifically, a reaction system including the aforementioned sample, the first substance carried by a solid carrier and specifically binding to an analyte and a second substance specifically binding to the analyte is formed, and the analyte is reacted with the first and second substances. Although the first and second substances may be simultaneously or successively reacted with the analyte, it is preferable to react them successively. In the former embodiment, for example, the first substance and the second substance are added to the sample. In the latter embodiment, the method comprises two reaction steps, for example, a first reaction step of adding the first substance to a sample and allowing them to react to form a first reaction product and a second reaction step of adding the second substance to the first reaction product and allowing them to react to form a second reaction product. In the present invention, the expression "to form a reaction system including a sample, a first substance and a second substance" thus include an embodiment in which the three components are reacted simultaneously (that is, comprising one reaction step) and an embodiment in which they are reacted successively (that is, comprising two reaction steps).

Following the first reaction step of reacting the analyte with the first substance to form the first reaction product, it is preferable to perform B/F separation (first separation step). Further, following the second reaction step of reacting the second substance with the first reaction product after the B/F separation to form the second reaction product, it is preferable to perform the second B/F separation (second separation step). With these procedures, measurement can be performed with further higher sensitivity. Conditions in each of these steps can be suitably selected depending on the combination of an analyte and substances specifically binding to it.

Specifically, for example, when antibodies and antigens are reacted and the amount of the reaction product is measured, the measurement can be performed as follows. That is, antigens or antibodies contained in whole blood are mixed with a solid carrier carrying antibodies or antigens specifically binding to them (first substance) and another kind of labeled antibodies or antigens (second substance) to form immune complexes. Then, unreacted antibodies and antigens are removed by washing (B/F separation), and the amount of the labeled substance bound to the solid carrier is measured. More specifically, for example, a sample containing whole blood and magnetic particles (solid carrier) carrying the first substance are placed in a reaction vessel and stirred, and then the antigen-antibody reaction is allowed at a predetermined temperature for predetermined time. Following the reaction, unreacted substances are removed from the reaction vessel by B/F separation utilizing a magnetic force. Subsequently, the labeled second substance is placed in a reaction vessel, reacted at a predetermined temperature for predetermined time and subjected to B/F separation utilizing a magnetic force again to remove unreacted substances. Finally, the analyte amount can be measured by measuring the amount of the labeled substance contained in the produced reaction product.

The solid carrier is not particularly limited so long as it is substantially insoluble in various solutions used in the measurement. However, magnetic particles and polymers such as polystyrene or latex thereof, gelatin, liposome and the like are preferably used. Among these, magnetic particles are particularly preferred in view of realization of quick and simple B/F separation. Specific examples thereof include magnetic particles composed of micro particles of metals such as triiron tetraoxide ($Fe_3O_4$), diiron trioxide ($Fe_2O_3$), various ferrites, iron, manganese, nickel, cobalt and chromium, alloys of cobalt, nickel, manganese and so forth. Further, it is also preferable to use these magnetic particles prepared so as to be contained in latex of polymers such as polystyrene, gelatin, liposome or the like or immobilized on surfaces of such materials.

Particle sizes of these solid carriers are not particularly limited so long as the B/F separation can be precisely performed. However, an unduly small particle size results in poor separation efficiency, and hence aggregation easily occurs. On the other hand, an unduly large particle size easily results in sedimentation. Therefore, the lower limit of the particle size is 0.05 μm, preferably 0.1 μm, and the upper limit is suitably 10 μm, preferably 4 μm, more preferably 2 μm. The particle size range is defined by a combination of these upper limits and lower limits. The specific particle size range of the carrier is usually 0.05 to 10 μm, preferably 0.05 to 4 μm, more preferably 0.1 to 2 μm.

The first substance specifically binding to an analyte can be carried by such solid carriers using conventional methods known per se. Specifically, for example, chemical bonding methods, physical adhesion methods and so forth can be mentioned.

The B/F separation in the measurement method using the solid carrier prepared as described above can be performed by filtration methods, antibody capture techniques, precipitation methods and the like. In particular, when magnetic particles are used, the B/F separation can be quickly and conveniently performed by generating a magnetic field with a permanent magnet, electromagnet or the like to utilize a magnetic force.

The measurement method of the present invention is a method characterized in that (1) the aforementioned reaction step is performed under a state that blood cells are not disrupted, and (2) at least the reaction step is preformed in the presence of a sufficient amount of a detergent that does not cause hemolysis, does not inhibit the reactions of the analyte with the first and second substances specifically binding to the analyte and can prevent influence of a component existing in the reaction system on the reaction system.

The expression "a state that blood cells are not disrupted" is not limited so long as the reaction step can be performed without disrupting blood cells in whole blood. This state means a state that blood cells are not disrupted or a small number of blood cells are disrupted to such an extent that the measurement should not be affected. As means for realizing the state that blood cells are not disrupted, there can be mentioned a method of adding a detergent that does not cause hemolysis in the reaction system, a method of regulating osmotic pressure of the reaction system with an isotonic solution such as physiological saline, a method of adding magnesium ions or the like to the reaction system to prevent disruption of cell nuclei and so forth. Further, these methods may be used in combination.

The detergent used in the present invention is not particularly limited so long as it is of a concentration and type that do not cause hemolysis, does not inhibit reactions of an analyte and first and second substances specifically binding to the analyte and can prevent influence of a component existing in a reaction system on the reaction system. The expression "do not cause hemolysis" used herein means that it does not cause hemolysis or the hemolysis is so weak that the measurement is not affected when the detergent is mixed with a sample containing whole blood. The expression "do not inhibit reactions of an analyte and first and second substances specifically binding to the analyte" means that the detergent does not inhibit formation of a reaction product by biochemically specific binding of these substances, or the inhibition is so weak that the measurement is not affected. The expression "prevent influence of a component existing in a reaction system on the reaction system" means that the detergent suppresses non-specific aggregation, adhesion on the inner wall of a reaction vessel or a pipette tip, bindings other than objective specific bindings and so forth caused by blood cells, other components or the like existing in the reaction system to prevent influence thereof during the reaction step.

By adding a detergent to the reaction system as described above, hemolysis can be prevented, non-specific adhesion of solid carriers such as magnetic particles on the inner wall of a reaction vessel or a pipette tip can be prevented, and influence caused by blood cell components and blood cells can be avoided during the measurement, and thereby a precise measurement can be performed.

In the present invention, polyoxyethylene sorbitan ester type or sulfobetaine type detergents are particularly preferably used.

Examples of the polyoxyethylene sorbitan ester type detergents include polyoxyethylene sorbitan monolaurate (Tween 20), polyoxyethylene sorbitan monooleate (Tween 80) and so forth. Among these, polyoxyethylene sorbitan monooleate (Tween 80), which has weak hemolysis action, is desirably used.

Examples of the sulfobetaine type detergents include dimethylethylammonium propanesulfonate, 3-(1-pyridino)-1-propanesulfonate, dimethylbenzylammonium propanesulfonate, n-octyl-N,N-dimethyl-3-ammonio-1-propanesulfonate, n-decyl-N,N-dimethyl-3-ammonio-1-propanesulfonate, n-dodecyl-N,N-dimethyl-3-ammonio-1-propanesulfonate, n-tetradecyl-N,N-dimethyl-3-ammonio-1-propanesulfonate, n-hexadecyl-N,N-dimethyl-3-ammonio-1-propanesulfonate and so forth. Among these, dimethylethylammonium propanesulfonate, 3-(1-pyridino)-1-propanesulfonate, dimethylbenzylammonium propanesulfonate and n-octyl-N,N-dimethyl-3-ammonio-1-propanesulfonate, which have weak hemolysis action, are particularly desirably used.

These detergents may be mixed with whole blood by adding them to the whole blood treatment solution as a pretreatment prior to the reaction step of forming a reaction system including a sample and first and second substances specifically binding to an analyte contained in the sample and reacting the analyte and the first and second substances. However, since the aforementioned detergents do not substantially inhibit the reactions of the analyte and the first and second substances specifically binding thereto, for example, when a solution of antibodies immobilized on a solid phase is used as the first substance carried by the solid carrier, the detergents may be added to the solution beforehand so as to allow the solution to directly react with the sample containing whole blood. Further, it is sufficient that the detergents are added at least during the first reaction step, in which many blood cells are contained in the reaction mixture. However, because they also have an effect of inhibiting non-specific adhesion or aggregation of the solid carrier, the detergents are preferably also added during the second reaction step. They may be added during all the steps including the measurement step.

Such detergents may be added at any concentration so long as they are added at such a concentration that the aforementioned effects should be exerted. Specifically, they are added at a final concentration during the reaction step in the range of, for example, 0.1 to 10%, preferably 0.5 to 5%, more preferably 0.5 to 2%. One type of such detergents may be solely used, or a mixture of two or more types may be used. When two or more types are used, they can also be used in an arbitrary combination at a concentration in such a range that the aforementioned effects should be exerted. Further, when the detergent is used in a whole blood treatment solution, the solution whole blood treatment can be prepared so that the detergent concentration in the solution should be in the range of 0.1 to 50%, preferably 0.5 to 30%, and used. The mixing ratio of the whole blood treatment solution containing a detergent, which is prepared as described above, and whole blood may be such a ratio that the detergent should have a concentration in the aforementioned concentration range in the sample containing whole blood after the mixing. Further, the mixing ratio is preferably determined in consideration of the amount of the analyte contained in the sample. When a trace amount substance contained in the sample in a small amount is to be measured, the proportion of the whole blood treatment solution is preferably determined to be small. Specifically, for example, the mixing ratio of whole blood and the whole blood treatment solution may be in the range of 99:1 to 5:95.

The whole blood treatment solution used in the present invention may be arbitrarily selected and used so long as the solution is in such an amount or has such a characteristic that blood cell components in whole blood should not be hemolyzed, or various components should not be denatured. Specific examples thereof include solutions adjusted to physiological pH, osmotic pressure, salt concentration and so forth, such as phosphate buffer (phosphate-buffered saline; PBS), physiological saline and physiological salt solutions. Further, any solution other than the solutions prepared as described above may also be mixed so long as it is in such an amount that blood cell components and other components should not be affected. However, if the analyte is a substance contained in the whole blood only in an extremely small amount, the measurement is preferably performed with whole blood itself or whole blood mixed with a whole blood treatment solution at a low mixing proportion.

The second substance is preferably labeled. Examples of the labeling substance include enzymes, luminescent substances, fluorescent substances, radioactive isotopes, coloring substances, various colored particles and so forth. Among these, enzymes are preferably used. Examples of enzymes often used in chemiluminescence enzyme immunoassay (CLEIA) include alkaline phosphatase, peroxidase, galactosidase, glucoxidase and so forth. As substrates of these enzymes, those corresponding to these enzymes can be selected. For example, there can be used adamantylmethoxyphenylphosphoryldioxetane (AMPPD) for alkaline phosphatase, luminol/peroxide for peroxidase, and adamantylmethoxyphenyl-$\beta$-D-galactosyldioxetane (AMPGD) for galactosidase.

As the measurement method of the reaction product, any conventional method known per se may be used. For example, when the second substance labeled as described above is used, the measurement can be conveniently performed by measuring the amount of the labeled substance in the reaction product. For example, when chemiluminescence enzyme immunoassay (CLEIA) is used, luminescence intensity of the labeled substance in the reaction product can be measured by using a photomultiplier tube (PMT) or the like.

That is, in the present invention, the expression "measuring a reaction product" means not only the direct measurement of the amount of the reaction product itself, but also includes the measurement of the amount of substances quantitatively related to the amount of the reaction product. The amount of an analyte to be measured in the specimen can be calculated from the amount of the reaction product measured as described above. Further, qualitative measurement for determining the presence or absence of the reaction product also falls within the scope of the measurement of the reaction product according to the present invention.

Further, when whole blood is used for the measurement, hematocrit correction is generally required after the measurement. In most samples, hematocrit values become about 40 to 50%. Further, when qualitative measurement is performed as a measurement item for positive or negative determination as in the case of infection diseases, hematocrit correction is not so important. Therefore, there is no practical problem even when the hematocrit value is not measured for each specimen. When the hematocrit value is available, a more precise assay result can of course be obtained by performing hematocrit correction [assay result× 100/(100−hematocrit value (%))].

The reagent kit of the present invention is a reagent kit for measuring an analyte in whole blood, which comprises a first substance carried by a solid carrier and specifically binding to the analyte, a second substance specifically binding to the analyte and a detergent which does not cause hemolysis and inhibit reactions of the analyte with the first substance and the second substance when it is mixed with the whole blood. The kit of the present invention is provided with the same configuration as that of conventional kits for measuring an analyte in plasma or serum except that the aforementioned detergent is included. That is, the reagent kit of the present invention is used in the aforementioned measurement method of the present invention.

The reagent kit preferably further includes a whole blood treatment solution. The whole blood treatment solution may contain such a detergent as described above. As arbitrary components, the reagent kit may further include a reaction diluent, substrate solution, substrate dissolving solution, washing solution, reaction terminating solution and so forth. By using such a reagent kit, the measurement method of the present invention can be quickly and conveniently performed with good precision and stability.

The measurement method of the present invention can be performed by using instruments, cartridges and so forth for automatic measurement known per se. Specific examples thereof include the cartridges and instruments described in WO01/84152, Japanese Patent Laid-open Publication No. 11-316226 and so forth. Further, the reagent kit of the present invention is also packaged in such a cartridge for automatic measurement and suitably used in the aforementioned automatic measurement instruments. By using the reagent kit of the present invention in combination with such instruments and cartridges for automatic measurement, a quick, convenient and highly sensitive measurement method can be provided

BEST MODE FOR CARRYING OUT THE INVENTION

The present invention will be explained more specifically with reference to the following examples. However, the scope of the present invention is not limited by these examples.

EXAMPLE 1

Preparation of Hepatitis B Virus Surface Antigen (HBsAg) Chemiluminescence Enzyme Immunoreagents (1) Preparation of Magnetic Particles Anti-HBsAg polyclonal antibodies were physically adhered on magnetic particles (0.3 μm) in 50 mM phosphate buffer (pH 4.0) and then treated with Tris buffer (0.1 M, pH 8.0) containing 0.2% BSA at 37° C. for 1 day to produce anti-HBsAg antibody-bound particles. The produced magnetic particles were suspended in 0.1 M Tris buffer (pH 8.0) at a concentration of 100 to 200 μg/ml.

(2) Preparation of Labeled Antibodies

Anti-HBsAg monoclonal antibodies were conjugated to bovine alkaline phosphatase (ALP) by the maleimide method to produce ALP-labeled anti-HBsAg antibodies. The produced labeled antibodies were suspended in 0.1 M Tris buffer (pH 8.0) at a concentration of 0.2 to 0.5 μg/ml and used.

(3) Preparation of B/F Washing Solution 0.1 M Tris buffer containing 1% Tween 20 and 0.15 M NaCl (pH 8.0) was prepared.

(4) Luminescence Substrate

As a luminescence substrate, 25 mM AMPPD solution (Tropix) was used.

EXAMPLE 2

Assay of Anti-HBsAg Antibody-Bound Particles and Labeled Antibodies

First, performance of the reagents produced in Example 1 was confirmed. The performance was evaluated by using HBsAg positive control serum and negative control serum as specimens, not using whole blood. In the assay, 60 μl of the specimen was added with 150 μl of magnetic particles, stirred and incubated at 42° C. for 10 minutes. Then, the magnetic particles were collected by a magnet and washed with the B/F washing solution. Subsequently, the washed magnetic particles were added with 150 μl of labeled antibodies, stirred and incubated at 42° C. for 10 minutes again. Then, the magnetic particles were collected by a magnet and sufficiently washed with the B/F washing solution. Further, the washed magnetic particles were added with 200 μl of the AMPPD solution, sufficiently mixed and incubated at 42° C. for 5 minutes. Then, the luminescence intensity was measured by using a photomultiplier tube (PMT).

The above measurement was repeated for 12 days, and reproducibility among the daily measurements was examined. As a result, favorable results were obtained as shown in Table 1.

TABLE 1

|  |  | Luminescence intensity |
|---|---|---|
| Negative control serum | Mean | 257 |
|  | Standard deviation | 17 |
|  | CV (%) | 6.5% |
| Positive control serum | Mean | 43035 |
|  | Standard deviation | 1404 |
|  | CV (%) | 3.1% |

EXAMPLE 3

Examination of Whole Blood Treatment Solution

Examination was conducted on the assumption that a detergent was added to the reaction system by adding the detergent to a whole blood treatment solution beforehand. The whole blood treatment solutions were prepared by dissolving various detergents in 0.1 M Tris buffer (pH 8.0) containing 1% BSA and 0.15 M NaCl, and it was examined which detergent was suitable for the measurement method of the present invention.

Blood was collected by using an EDTA blood collection tube. Then, HBsAg was added at 1 U/ml to each of the whole blood stored at 4° C. for 3 days and plasma obtained from the whole blood by centrifugation, and a recovery test for HBsAg was performed using the luminescence intensity obtained in the measurement using plasma, which was taken as 100%. In the whole blood, blood cell components were precipitated during the storage at 4° C., and hemolysis was slightly observed in the plasma portion. The amount of the hemolyzed cells was measured by another method, and it was found that hemolysis occurred in about 5% of the total erythrocytes.

The assay was performed in the same manner as in Example 2. Whole blood and each of the various whole blood treatment solutions were mixed at a ratio of 9:1, plasma was mixed with purified water at a ratio of 9:1, and HBsAg was immediately measured. Further, whole blood was mixed with the aforementioned buffer (0.1 M Tris buffer (pH 8.0) containing 1% BSA and 0.15 M NaCl) without adding a detergent instead of a whole blood treatment solution, and HBsAg was measured in the same manner. Presence or absence of hemolysis in the reaction system, non-specific adhesion of magnetic particles on the reaction vessel (made of polypropylene) and non-specific aggregation of magnetic particles during reaction were confirmed by visual inspection. The results are shown in Table 2.

TABLE 2

| Specimen | Detergent concentration upon mixing of whole blood | Hemolysis | Adhesion of magnetic particles to reaction vessel wall | Aggregation of magnetic particles | Luminescence intensity | Recovery ratio |
|---|---|---|---|---|---|---|
| Triton X-100 | Whole blood | 1% | Present | Absent | Present | 5130 | 42% |
| Tween 20 | Whole blood | 1% | Absent | Absent | Absent | 10620 | 87% |
| Tween 80 | Whole blood | 1% | Absent | Absent | Absent | 10260 | 85% |
| 3-(1-Pyridino)-1-propanesulfonate | Whole blood | 2% | Absent | Trace amount | Absent | 10830 | 88% |
| Brij 78 | Whole blood | 1% | Present | Absent | Present | 5820 | 48% |
| Saponin | Whole blood | 1% | Present | Significant | Present | 9460 | 77% |
| SDS | Whole blood | 1% | Present | Absent | Present | 2450 | 20% |
| CHAPS | Whole blood | 1% | Present | Absent | Present | 8020 | 66% |
| Without detergent | Whole blood | 0% | Absent | Significant | Significant | 11690 | 96% |
| Distilled water | Plasma | 0% | Absent | Absent | Absent | 12240 | 100% |

Triton X-100: Polyoxyethylene octyl phenyl ether
Tween 20: Polyoxyethylene sorbitan monolaurate
Tween 80: Polyoxyethylene sorbitan monooleate
Brij 78: Polyoxyethylene stearyl ether
SDS: Sodium dodecylsulfate
CHAPS: 3-{(3-Cholamidopropyl)dimethylammonio}-1-propanesulfonate As shown in Table 2, when whole blood was used as a sample, the measurement results for the recovery ratio were 85% or higher in the samples mixed with Tween 20, Tween 80 or 3-(1-pyridino)-1-propanesulfonate, or a sample not containing a detergent (0.1 M Tris buffer (pH 8.0) containing 1% BSA and 0.15M NaCl). Among these, the recovery ratio of the sample not containing a detergent appeared favorable. However, a very large amount of magnetic particles were adhered on the inner wall of the reaction vessel, thus B/F washing was not performed well, and therefore it could not be considered that correct assay results had been obtained. Therefore, the samples mixed with Tween 20, Tween 80 and 3-(1-pyridino)-1-propanesulfonate were further examined thereafter.

Further, it was demonstrated in this experiment that, by using the technique described above, concentrations and types of detergents not causing substantial hemolysis, not inhibiting reactions of an analyte and substances specifically binding to the analyte and capable of preventing influence of components existing in the reaction system on the reaction system in an objective reaction system could be easily selected from various detergents.

EXAMPLE 4

Examination of Types and Concentrations of Detergents by Using Whole Blood

Blood was collected by using a blood collection tube treated with heparin as an anticoagulant. HBsAg was added at 0.5 U/ml each to the whole blood stored overnight at 4° C. and plasma obtained from it, and an addition and recovery test was performed in the same manner as in Example 3 using the luminescence intensity in plasma, which was taken as 100%. For whole blood treatment solutions, Tween 20, Tween 80 and 3-(1-pyridino)-1-propanesulfonate selected in Example 3 as well as Triton X-100 for comparison were used. Each detergent was added at a concentration of 0.01, 0.1, 0.5, 1 and 10% as a final concentration after the mixing with whole blood. Presence or absence of hemolysis in the reaction system, non-specific adhesion of magnetic particles on the reaction vessel (made of polypropylene) and non-specific aggregation of magnetic particles during reaction were confirmed by visual inspection for each detergent in each reaction system, and recovery ratio with respect to the added amount was determined. The results are shown in Table 3.

From the assay results, detergents providing a favorable recovery ratio with respect to the added amount without causing hemolysis or non-specific adhesion of magnetic particles on the reaction vessel were selected. As a result, particularly favorable results were obtained when Tween 80 was added at a concentration of 0.5 to 10%, or 3-(1-pyridino)-1-propanesulfonate was added at a concentration of 1%. When Triton X-100 was added at a concentration of 0.5%, hemolysis was observed, although the recovery ratio was 75%, which was generally favorable. Further, when Tween 20 was added at a concentration of 1 to 10%, sufficient recovery ratio with respect to the added amount could not be obtained, although hemolysis and non-specific adhesion of magnetic particles on the reaction vessel were not observed.

TABLE 3

| Specimen | | Detergent concentration upon mixing of whole blood (%) | Hemolysis | Adhesion of magnetic particles to reaction vessel wall | Aggregation of magnetic particles | Luminescence intensity | Recovery ratio |
|---|---|---|---|---|---|---|---|
| Triton X-100 | Whole blood | 0.01 | Absent | Present | Present | 1084 | 19% |
| Triton X-100 | Whole blood | 0.1 | Absent | Present | Present | 1424 | 25% |

TABLE 3-continued

| Specimen | Detergent concentration upon mixing of whole blood (%) | Hemolysis | Adhesion of magnetic particles to reaction vessel wall | Aggregation of magnetic particles | Luminescence intensity | Recovery ratio |
|---|---|---|---|---|---|---|
| Triton X-100 | Whole blood | 0.5 | Present | Absent | Present | 4288 | 75% |
| Triton X-100 | Whole blood | 1 | Present | Absent | Present | 2800 | 49% |
| Triton X-100 | Whole blood | 10 | Present | Absent | Present | 1422 | 25% |
| Tween 20 | Whole blood | 0.01 | Absent | Present | Present | 992 | 17% |
| Tween 20 | Whole blood | 0.1 | Absent | Present | Present | 1268 | 22% |
| Tween 20 | Whole blood | 0.5 | Absent | Present | Present | 2696 | 47% |
| Tween 20 | Whole blood | 1 | Absent | Absent | Absent | 3520 | 62% |
| Tween 20 | Whole blood | 10 | Absent | Absent | Absent | 2368 | 42% |
| Tween 80 | Whole blood | 0.01 | Absent | Present | Present | 1304 | 23% |
| Tween 80 | Whole blood | 0.1 | Absent | Present | Present | 1436 | 25% |
| Tween 80 | Whole blood | 0.5 | Absent | Absent | Present | 4256 | 75% |
| Tween 80 | Whole blood | 1 | Absent | Absent | Absent | 4564 | 80% |
| Tween 80 | Whole blood | 10 | Absent | Absent | Absent | 5180 | 91% |
| 3-(1-Pyridino)-1-propanesulfonate | Whole blood | 0.01 | Absent | Present | Present | 1596 | 28% |
| 3-(1-Pyridino)-1-propanesulfonate | Whole blood | 0.1 | Absent | Present | Present | 2920 | 51% |
| 3-(1-Pyridino)-1-propanesulfonate | Whole blood | 0.5 | Absent | Absent | Present | 2720 | 48% |
| 3-(1-Pyridino)-1-propanesulfonate | Whole blood | 1 | Absent | Absent | Absent | 4896 | 86% |
| 3-(1-Pyridino)-1-propanesulfonate | Whole blood | 10 | Present | Absent | Absent | 1272 | 22% |
| Distilled water | Whole blood | 0 | Absent | Present | Present | 788 | 14% |
| Distilled water | Plasma | 0 | Absent | Absent | Absent | 5696 | 100% |

EXAMPLE 5

Examination by Using Fresh Whole Blood

Subsequently, 3-(1-pyridino)-1-propanesulfonate and Tween 80 selected in Example 4 were examined by using fresh blood. In emergent tests, in particular, it is desirable to perform an assay immediately after blood collection, and erythrocytes in whole blood may be gradually hemolyzed during storage, possibly affecting the measurement. Therefore, examination was performed by using fresh blood immediately after blood collection. An addition and recovery test for HBsAg was performed in the same manner as in Example 3. Whole blood treatment solutions were prepared by adding 3-(1-pyridino)-1-propanesulfonate, Tween 80 and a mixture thereof. The results are shown in Table 4.

As a result of the measurement, favorable recovery ratio of 86 to 102% was obtained, even when fresh whole blood was used.

INDUSTRIAL APPLICABILITY

According to the method of the present invention, an analyte can be quickly and conveniently measured with high sensitivity by using whole blood as it is as a sample.

What is claimed is:
1. A method for measuring quantitatively or qualitatively an analyte in a whole blood sample, comprising:
forming a reaction system by mixing the whole blood sample with a whole blood treatment solution comprising detergent of the type that does not cause hemolysis, and adding to the mixture of the whole blood sample

TABLE 4

| Specimen | Detergent concentration upon mixing of whole blood (%) | Hemolysis | Adhesion of magnetic particles to reaction vessel wall | Aggregation of magnetic particles | Luminescence intensity | Recovery ratio |
|---|---|---|---|---|---|---|
| 3-(1-Pyridino)-1-propanesulfonate | Whole blood | 2% | Absent | Absent | Present | 11370 | 86% |
| Tween 80 | Whole blood | 1% | Absent | Absent | Absent | 13460 | 102% |
| 3-(1-Pyridino)-1-propanesulfonate + Tween 80 | Whole blood | 2% 1% | Absent | Absent | Absent | 12910 | 98% |
| Distilled water | Plasma | 0% | Absent | Absent | Absent | 13180 | 100% | and the whole blood treatment solution a first substance which is immobilized on a solid carrier and specifically binds to an analyte contained in the whole blood sample and a second substance which specifically binds to the analyte to allow the analyte to react with the first and second substances to form a complex of first substance-analyte-second substance, separating the complex, and detecting the complex to measure quantitatively or qualitatively the analyte in the complex, wherein said reaction system comprises the detergent in a concentration range of 0.5 to 5% so that hemolysis is prevented.

2. The method according to claim 1, wherein the detergent is selected from the group consisting of polyoxyethylene sorbitan ester type detergents and sulfobetaine type detergents.

3. The method according to claim 1, wherein the ratio of the whole blood sample and the whole blood treatment solution is in the range of 99:1 to 5:95.

4. The method according to claim 1, wherein the reaction system is formed by mixing the whole blood sample with a whole blood treatment solution comprising detergent, then adding the first substance to the mixture of the whole blood sample and the whole blood treatment solution, and then adding the second substance to the mixture of the whole blood sample, the whole blood treatment solution, and the first substance.

5. The method according to claim 1, wherein the second substance is labeled with a labeling substance.

6. The method according to claim 1, wherein the first and second substances which specifically bind to the analyte are an antigen or an antibody.

7. A reagent kit for measuring an analyte in a whole blood sample, which comprises a first substance which is immobilized on a solid carrier and specifically binds to the analyte, a second substance which specifically binds to the analyte, and a whole blood treatment solution which comprises detergent of the type that does not cause hemolysis, wherein said reaction system comprises the detergent in a concentration range of 0.5 to 5% so that hemolysis is prevented.

* * * * *

(12) EX PARTE REEXAMINATION CERTIFICATE (7301st)
United States Patent
Yokoi

(10) Number: US 7,338,809 C1
(45) Certificate Issued: Jan. 5, 2010

(54) METHOD FOR ASSAYING WHOLE BLOOD

(75) Inventor: Hiroyuki Yokoi, Tokyo (JP)

(73) Assignee: Mitsubishi Kagaku Iatron, Inc., Shinjuku-Ku, Tokyo (JP)

Reexamination Request:
No. 90/010,359, Dec. 16, 2008

Reexamination Certificate for:
Patent No.: 7,338,809
Issued: Mar. 4, 2008
Appl. No.: 10/657,118
Filed: Sep. 9, 2003

Related U.S. Application Data

(63) Continuation of application No. PCT/JP02/02139, filed on Mar. 7, 2002.

(30) Foreign Application Priority Data

Mar. 9, 2001 (JP) .................................... 2001-067360

(51) Int. Cl.
*G01N 1/00* (2006.01)

(52) U.S. Cl. .................... 436/176; 435/7.1; 435/7.25; 435/7.92; 435/7.94; 436/517; 436/518; 436/522; 436/524; 436/528; 436/538; 436/10; 436/17; 436/18; 436/166; 422/61

(58) Field of Classification Search .................. None
See application file for complete search history.

(56) References Cited

FOREIGN PATENT DOCUMENTS

JP 2000-131319 5/2000

*Primary Examiner*—Brenda Brumback

(57) ABSTRACT

In a method for measuring an analyte, which comprises a reaction step of forming a reaction system including a sample containing whole blood, a first substance carried by a solid carrier and specifically binding to an analyte contained in the sample and a second substance specifically binding to the analyte and allowing the analyte to react with the first and second substances and a measurement step of measuring the formed reaction product (1) the reaction step is performed in a state that blood cells are not disrupted, and (2) at least the reaction step is performed in the presence of a sufficient amount of a detergent that does not cause hemolysis, does not inhibit reactions of the analyte with the first and second substances specifically binding to the analyte and can prevent influence on the reaction system of a component existing in the reaction system.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–7 is confirmed.

* * * * *